United States Patent [19]

Masson et al.

[11] Patent Number: 4,749,466
[45] Date of Patent: Jun. 7, 1988

[54] SOLID ELECTROLYTE FOR OXYGEN SENSOR

[75] Inventors: Charles R. Masson; Philip D. Pacey, both of Halifax, Canada; Shi X. Dou, Liaonig, China

[73] Assignee: Canadian Patents and Development Limited, Ottawa, Canada

[21] Appl. No.: 40,246

[22] Filed: Mar. 26, 1987

[30] Foreign Application Priority Data

Oct. 10, 1986 [CA] Canada .................. 520282

[51] Int. Cl.$^4$ ............................ G01N 27/26
[52] U.S. Cl. ........................ 204/421; 204/427; 429/30; 429/33; 501/103; 501/104; 501/105
[58] Field of Search ............ 204/421, 424, 427; 429/30, 33; 501/103-105

[56] References Cited

U.S. PATENT DOCUMENTS

| | | | |
|---|---|---|---|
| 3,347,767 | 10/1967 | Hickam | 204/195 |
| 4,505,806 | 3/1985 | Yamada | 204/426 |
| 4,626,517 | 12/1986 | Watanabe et al. | 501/103 |

OTHER PUBLICATIONS

Viking Ceramics of 4591 Follenslev, Denmark.
Heyne and den Engelsen; J. Electrochemical Society, 124, 727–735, 1977.

Primary Examiner—John F. Niebling
Assistant Examiner—Kathryn Rubino

[57] ABSTRACT

The invention is based on the discovery that in a solid electrolyte galvanic sensor, e.g. an yttria-stablized zirconia body, it is not necessary, as has hitherto been believed, to eliminate all impurities to achieve the important performance characteristics of rapid response time, reduced susceptibility to aging, and improved reliability. It has now been found that these improvements can be obtained by reducing only the concentration of iron oxide (and any other variable valence oxides that sometimes occur) in the sample, and that it is unnecessary to lower the concentration of oxides of fixed valence elements, such as silicon, aluminum, magnesium, and the alkali and alkaline earth metals, many of which tend to occur frequently as impurities in ceramic materials. This inventive selective elimination of only the variable valence oxides saves substantial cost in manufacture without loss of the performance advantages mentioned above. Indeed, better mechanical properties are often obtained. In a specific example the invention provides a solid electrolyte in which the concentration of iron oxide, expressed as $Fe_2O_3$, and oxides of other variable valence elements, is less than 0.02 percent by weight, while the concentration of fixed valence oxides remains at least 0.5 percent by weight.

6 Claims, 1 Drawing Sheet

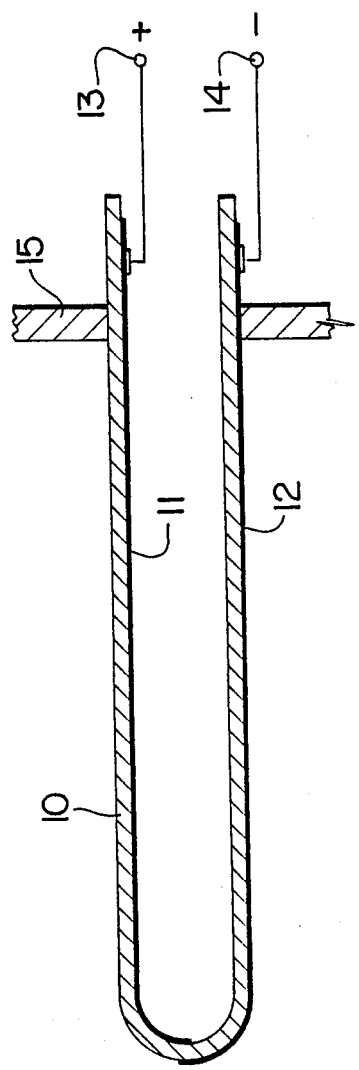

SOLID ELECTROLYTE FOR OXYGEN SENSOR

FIELD OF THE INVENTION

This invention relates to an improved solid electrolyte for use in an oxygen sensor.

Oxygen sensors based on the principle of solid electrolyte galvanic cells essentially contain an oxide-ion conductive ceramic body with electrodes in contact with opposite faces of the body. One electrode is exposed to a reference source of oxygen. The other electrode is exposed to a source whose oxygen content is to be determined. When the pressure or partial pressure of oxygen at the two electrodes is different, a potential is developed between them, which is the sensor output voltage.

BACKGROUND OF THE INVENTION

Such sensors have wide commercial and industrial application. To illustrate their use and to provide some indication of the significance of the invention the following examples are chosen. The list is by no means exhaustive and is given merely to illustrate a variety of applications of such sensors and to indicate the nature and scope of applicability of the invention.

1. Solid electrolyte ceramic sensors are used widely to monitor the oxygen content of the exhaust gas produced by an internal combustion engine. The sensor output voltage is used to regulate the efficiency of the engine by providing feedback to a device that controls the air-to-fuel ratio. In one type of such sensor, the solid electrolyte has the general shape of a thimble and is comprised of a stablized zirconia material, with platinum electrodes formed on the interior and exterior surfaces of the material. Typically, such a sensor operates at exhaust temperatures above 400° C. and requires some time to heat up before it becomes responsive. An auxiliary electrical heater may be incorporated in the sensor to overcome this limitation. An example of such a sensor, with an auxiliary heating element, is described in U.S. Pat. No. 4,175,019 issued Nov. 20, 1979 to Michael P. Murphy. Automobile sensors of this type are used extensively to reduce exhaust emissions and achieve fuel economy. Their response times and the temperatures at which they operate reliably are important features.

2. Solid electrolyte sensors may be used for the quantitative measurement of oxygen pressure inside a vacuum chamber over the range 1 to $10^{-7}$ Torr. An example of such a device, and its performance as a partial pressure oxygen gauge, has been given by C. J. Mogab, J. Vac. Sci. Technology 10, 852–858 (1973). Such a gauge normally operates at temperatures between 600° and 800° C. The low pressure limit is determined by the permeation of oxygen through the solid electrolyte. This not only alters the pressure that is to be determined, but causes departure of the sensor output voltage from the true value given by the well-known Nernst equation (see below).

3. An important application of electrochemical oxygen sensors is the determination of the concentration of oxygen in molten metals. See, for example, New Application of Oxygen Sensors to Ironmaking and Steelmaking in Japan by K. Kagata et al published in Transactions ISIJ 25, 204–211(1985); and Progress of Chemical Sensors with Solid Electrolytes at High Temperature by K. S. Goto published in Proceedings of International Meeting on Chemical Sensors, Fukuoka, Japan, Sept. 19–22, 1983. Typically, such sensors operate at temperatures in the range 700° to 1600° C., depending on the metal whose oxygen content is to be determined. In devices of this nature the solid electrolyte is often in the form of a pellet that is sealed or embedded into one end of a ceramic or quartz tube. For the determination of oxygen in liquid steel, where temperatures of about 1600° C. and highly corrosive conditions are encountered, such devices are usually operated as disposable probes. The pelleted end of the tube is plunged into the liquid metal and the sensor output voltage is recorded continuously until failure of the probe occurs. The output voltage at the moment of failure is then generally accepted as the true output voltage corresponding to the oxygen content of the liquid metal. Such sensors depend for their reliability on a fast response of the output voltage to rapid changes in temperature.

4. Other major applications of solid electrolyte sensors are in the glass and ceramic industries as, for example, in monitoring the oxygen content of molten glass or in monitoring the partial pressure of oxygen in ceramic kilns to control the color of glazes. They are also used in direct reduction kilns for the production of iron, in copper smelting reverbatory furnaces, and in furnaces for the heat-treatment of metals as, for example, in gas carburizing for the hardening of metal surfaces. They are also used extensively to measure the oxygen content of boiler flue gases. They may be employed as safety devices in which the sensor output voltage is connected to an alarm system to warn of impending explosive mixtures if a combustion process fails.

By constant monitoring and controlling the atmosphere in such processes, considerable savings in fuel can be effected. The location of the probe is often an important consideration. In some applications, for example, it may be desirable to locate the sensor close to a flame, to indicate the partial pressure of oxygen in the combustion gases at that point. In other applications it may be desirable to locate the sensor at a position remote from the source of combustion as, for example, in a flue or stack, to indicate the average partial pressure of oxygen in the products of combustion. The probes should thus be capable of responding accurately over a wide range of temperatures and/or oxygen pressures. Such probes may also have to retain their operating characteristics over periods of months or even years of service and it is important in such cases that the probe should not be susceptible to what is commonly termed aging, i.e. changes in the sensor output voltage over prolonged usage. The time of response of the probe to rapid changes in pressure or partial pressure of oxygen is important in many applications. The passage of oxygen through the probe should be minimal, so that the sensor output voltage corresponds closely to the true value for the oxygen pressure or concentration to be determined.

PRIOR ART

Most solid electrolyte galvanic sensors for the determination of oxygen are composed of a basic component consisting of an oxide of a tetravalent element, such as zirconia, thoria or hafnia, which is "doped" with a smaller amount of a second oxide of an element of lower valence, such as lime, magnesia or yttria, which latter oxide enters into solid solution with the basic oxide. Because of the different valences of the two metallic elements in the mixed oxide, there is a deficiency of oxide anions in the oxidic or anionic part of the crystalline lattice of which the solid solution is comprised. This deficiency, the extent of which depends on the concentration of "dopant" oxide, results in the formation of vacant positions or vacant sites in the anionic lattice portion of the mixed oxide. These vacant sites are also referred to as anion vacancies.

When the two faces of the solid electrolyte body are respectively brought into contact with the reference source of oxygen and the source whose oxygen content is to be determined, there is a tendency for the oxygen in the source of higher oxygen pressure to enter the electrolyte as oxide ions by acquiring electrons and occupying vacant lattice sites. This tendency may be represented by the equation

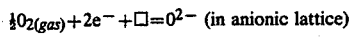
$$\tfrac{1}{2}O_{2(gas)} + 2e^- + \square = O^{2-} \text{ (in anionic lattice)}$$

where $e^-$ represents an electron and $\square$ represents a vacant lattice site.

Similarly, at the face of the electrolyte exposed to the source of lower oxygen pressure there is a tendency for oxide ions in the anionic lattice to lose electrons and enter the gaseous phase, leaving behind an anion vacancy. This may be represented by the equation

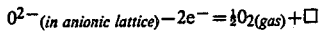
$$O^{2-}_{\text{(in anionic lattice)}} - 2e^- = \tfrac{1}{2}O_{2(gas)} + \square$$

where the symbols have the same significance as before.

The net result of these two tendencies is that the surface of the electrolyte exposed to the source of higher oxygen pressure develops a negative electrical potential relative to the surface exposed to the source of lower oxygen potential and this is the origin of the sensor output voltage.

For a perfect sensor there is no passage of oxygen through the electrolyte. The sensor output voltage is a measure only of the tendency of oxygen to migrate from the region of higher to lower oxygen pressure. The voltage acts in such a manner as to oppose the passage of oxide ions from one face of the electrolyte to the other. In a perfect electrolyte the output voltage is a true measure of the ratio of oxygen pressures on the two sides of the electrolyte and is given by the Nernst equation $$E = \frac{RT}{4F} \log_e \frac{PO_2(1)}{PO_2(2)}$$

where E is the sensor output voltage, R is the gas constant, T is the temperature in degrees Kelvin, F is the Faraday constant and $PO_2(1)$ and $PO_2(2)$ are the oxygen pressures on the two sides of the electrolyte.

A perfect electrolyte is one that conducts electricity only by the passage of ions. It does not allow the passage of electrons, i.e. it has no electronic conductivity. In practice, electronic conduction is nearly always present to some extent in solid oxide electrolytes and becomes more important at higher temperatures and lower oxygen pressures. It is an intrinsic property of the electrolyte material. However, for most practical purposes it is so small that it can be ignored, provided that the sensor is operated in the region of temperature and oxygen pressure referred to as the ionic domain.

Electronic conduction in the electrolyte is also influenced by the presence of impurities. When electronic conduction is present to a significant extent the sensor output voltage is no longer equal to the true value given by the Nernst equation, but is smaller than the true value. This is due to the passage of electrons, or flow of current, through the electrolyte, caused by the voltage difference between its faces. The situation is analogous to an electrochemical cell in which there is an internal short circuit. The flow of electrons is accompanied by the passage of oxygen ions through the electrolyte and, if the system is isolated, the cell runs down or becomes discharged.

For oxygen to pass spontaneously through the electrolyte, therefore, two conditions must be fulfilled. First, oxygen must dissolve in the electrolyte by acquiring electrons, so that it may enter the electrolyte as negatively charged oxide ions. Second, it must move through the electrolyte by virtue of electronic conduction in the electrolyte.

It has been appreciated by some manufacturers that the response time and aging characteristics of solid electrolyte oxygen sensors are dependent on the impurities present in the electrolyte, and that absence of impurities results in faster response times and eliminates the aging characteristic. For example, the ceramics manufactured by Viking Ceramics, of 4591 Follenslev, Denmark, are reported as having typical impurity contents of Si 0.001%, Al 0.001%, Na 0.002%, Ca 0.002% and Fe 0.001%. This manufacturer draws attention to the very low silica content, claiming that this key impurity has a profound influence on the electrical properties of zirconia ceramics, and further claiming that his low impurity product provides an extremely fast response in oxygen analyzer applications. Similarly, William M. Hickam in U.S. Pat. No. 3,347,767 issued Oct. 17, 1967 discloses an electrolyte material, $(ZrO_2)_{0.8}(CaO)_{0.2}$ with no more than a few tenths of one percent of impurities, resulting, it is claimed, in negligible electronic conductivity.

Many impurities normally occur naturally in zirconia, the preferred basic oxide, and the elimination of these impurities is costly.

L. Heyne and D. den Engelsen (J. Electrochem. Soc., 124, 727–735 (1977)) have discussed the factors that affect the speed of response of solid electrolyte gas sensors and have concluded that the uptake or release of gas by the electrolyte is the main reason for sluggishness in response and for variation with time of the sensor output voltage.

SUMMARY OF THE INVENTION

The present inventors agree with this latter conclusion, and have demonstrated for the first time that it is the concentration of oxides of variable valence elements, especially iron oxide, that is responsible for the uptake or release of gas. The solubility of oxygen in iron-free samples has been found to be negligible, notwithstanding significant levels of impurities of oxides of fixed valence elements.

As a consequence of this discovery, the present invention enables the achievement of an improved solid electrolyte ceramic body that has the desired performance (fast response, reliability, and resistance to aging), while avoiding the disadvantage of requiring the costly elimination of many of the other impurities that have now been found to have no appreciable influence on performance.

More specifically, the inventors have discovered that an oxygen gas sensor ceramic body having a faster response to changes in oxygen pressure and temperature, a more reliable performance at lower operating temperatures and oxygen pressures, an improved resistance to aging, and a lower permeability to oxygen, can be produced by maintaining in the electrolyte a concentration of iron oxide and other variable valence oxide impurities, such as the oxides of copper, cobalt, chromium or nickel, at a lower level than has hitherto been commonly employed, without changing the concentration of the oxides of other elements that are commonly present, such as silicon, aluminum, magnesium, the alkali or alkaline earth metals, which are of fixed valence.

In particular, the invention relates to sensors in which the concentration in the electrolyte of the aggregate of variable valence oxides (in practice, mostly $Fe_2O_3$) is less than 0.02 percent by weight, while the concentration of fixed valence oxide impurities are maintained at conventional levels, i.e. at least 0.5% by weight and more often between 1.0 and 2.5%. The above percentage for $Fe_2O_3$ is significantly lower than the values of 0.1 to 0.2 percent by weight that are commonly present in most commercial electrolytes.

Hence, the characterising feature of the invention is the discovery that in order to improve the quality of the sensor it is only the variable valence oxide impurities, of which the most commonly occurring are the oxides of iron, that must be reduced to a lower concentration than has hitherto been generally employed, and not the oxide impurities of the fixed valence elements.

This new knowledge provides for the preparation of solid electrolyte ceramic bodies with improved performance at a lower cost.

Moreover, it provides for the preparation of solid electrolyte ceramic bodies that achieve the improved performance without sacrifice of mechanical properties. In other words, according to the invention, the response time, resistance to oxygen permeation and aging characteristics of a sensor employing such a ceramic body can be improved without altering the ease of fabrication, mechanical strength, thermal shock stability or other physical or chemical properties of the ceramic electrolyte, which properties often depend on the presence of oxides of fixed valence elements, such as silica and alumina, whether present as impurities in the starting materials or added deliberately during the fabrication process.

Specifically, the inventors' research has shown, for the first time, that the solubility of oxygen in stabilized zirconia electrolytes is markedly dependent on the concentration of iron oxide in the electrolyte, this being the main factor that controls the solubility of oxygen. In the absence of iron oxide and oxides of other elements of variable valence, the solubility of oxygen in limestabilized zirconia was found to be so small that it was undetectable. Deliberate addition of iron oxide to the electrolyte, however, increased the solubility in proportion to the amount added.

Of particular interest in this connection is the recent work by M. Sasabe and Y. Kinoshita (Trans. Iron and Steel Institute, Japan, 20, 801-809 (1980)) on the transport of oxygen through metallurgical slags in which it was shown that the permeability of oxygen through molten slags containing lime, silica and alumina was raised by a factor of the 10th power of 10 (i.e. a factor of $10^{10}$ or ten billion) when only 0.2 weight percent of $Fe_2O_3$ was added to the slag.

The inventors' research has also shown that the rate of response of the sensor output voltage to changes in temperature and oxygen pressure is dependent on the solubility of oxygen in the electrolyte. When the temperature or the pressure of oxygen in contact with one or both faces of the electrolyte is suddenly altered, time is required for the amount of oxygen dissolved in the electrolyte to re-adjust to the new condition. It has clearly been shown that it is this factor, namely the amount of dissolved oxygen or "excess oxygen" in the electrolyte, that determines its speed of response.

BRIEF DESCRIPTION OF THE DRAWING

The drawing shows a sectional view of an oxygen sensor embodying a solid electrolyte ceramic body.

DETAILED DESCRIPTION OF THE EMBODIMENT

This ceramic body is in the form of a yttria-stabilized (5.24% yttria) tube 10 closed at one end and electrodes 11 and 12 which consist of narrow platinum strips deposited on the inner and outer surfaces of the tube. These strips are connected by means of terminals 13 and 14 to a voltage measuring device (not shown). In this particular form of sensing device the ceramic tube is shown as passing through a wall 15 of a combustion chamber or exhaust manifold. The outer surface of the ceramic tube is exposed to the gases within the chamber or manifold, whose oxygen content is to be determined. The inner surface is exposed to air as the reference gas. With a device of this nature, when the pressure of air outside the tube was changed suddenly from 757 to 22.2 Torr, the time required for the sensor output voltage to change by one half of the theoretical value as calculated from the Nernst equation was 225 milliseconds at 650° C. and 667 milliseconds at 618° C. The concentration of $Fe_2O_3$ in this tube was 0.1 percent by weight, i.e. a typical prior art concentration. The inventors then constructed another tube 10 that was identical in all other respects but which contained only 0.008 weight percent of $Fe_2O_3$. The corresponding response times were 28 and 98 milliseconds, i.e. approximately 7 to 8 times faster, and hence proof that the concentration of iron oxide is responsible for the response speed. Typical fixed valence oxide impurities in the tube 10 are $Al_2O_3$-0.2%; $SiO_2$-0.4%; $TiO_2$-0.2% and $Na_2O$-0.02% and possibly some small amounts of others, for a total of at least about 0.82%.

Rather than take the form shown in the drawing, a sensor according to the present invention can take many other physical forms, for example, as disclosed in
(a) Sensor for On-Vehicle Detection of Engine Exhaust Gas Composition by William J. Fleming et al published in Society of Automotive Engineers Transactions Vol. 82, 1973 p.1969-1984;
(b) The $SIRO_2$ Solid Electrolyte Oxygen Sensor published by CSIRO, Australia, June 1979;
U.S. Pat. No. 4,251,342 issued Feb. 17, 1981 to E. P. Habdas et al;
(d) A Zirconia-Based Lean Air-Fuel Ratio Sensor by David S. Howarth et al published in Society of Autotive Engineers Technical Paper Series 780212;
(e) Sensors for automotive application by M. H. Westbrook published in J. Phys. E:Sci. Instrum. Vol. 18, 1985;
(f) Some New Applications for Zirconia Sensors by J. A. Brothers et al published in Mechanical Engineering 102, 35-37(1980);
U.S Pat. No. 3,768,259 issued Oct. 30, 1973 to R. D. Carnahan et al; or
U.S. Pat. No. 4,129,099 issued Dec. 12, 1978 to D. S. Howarth.

To summarise the invention, while the presence of impurities has been known for many years to be important for performance, it has been thought prior to the present invention that all the impurities needed to be eliminated in order to achieve a fast response. In contradistinction, the present invention is based on the discovery that it is a lack of iron oxide (or other variable valence oxide impurities) that is alone responsible for the fast response and the other desirable performance characteristics mentioned above.

We claim:

1. A solid electrolyte ceramic body comprising an oxide of a tetravalent element selected from the group consisting of zirconia, thoria and hafnia, doped with an oxide of an element of less valence than four selected from the group consisting of yttria, lime and magnesia, wherein the weight percentage of impurities of all oxides of variable valence elements combined is no greater than 0.02, while the weight percentage of all oxides of fixed valence elements combined is at least 0.5%.

2. A solid electrolyte ceramic body according to claim 1, wherein the weight percentage of impurities of all oxides of variable valence elements combined is no greater than 0.008.

3. A solid electrolyte ceramic body according to claim 1 or 2, wherein the weight percentage of all oxides of fixed valence elements combined is at least 1.0%.

4. A solid electrolyte ceramic body according to claim 1 or 2, wherein the oxides of variable valence elements consist predominantly of iron oxide.

5. A solid electrolyte ceramic body according to claim 1 or 2, wherein the oxides of fixed valence elements consist predominantly of silica and alumina.

6. An oxygen sensor comprising
 (a) a solid electrolyte ceramic body according to claim 1 or 2, and
 (b) a pair of electrodes on respective surfaces of said body, for generating a voltage across said electrodes on exposure of said surfaces to respective atmospheres having oxygen concentrations different from each other.

* * * * *